(12) United States Patent
Daimon

(10) Patent No.: US 6,690,007 B2
(45) Date of Patent: Feb. 10, 2004

(54) THREE-DIMENSIONAL ATOM MICROSCOPE, THREE-DIMENSIONAL OBSERVATION METHOD OF ATOMIC ARRANGEMENT, AND STEREOSCOPIC MEASURING METHOD OF ATOMIC ARRANGEMENT

(75) Inventor: Hiroshi Daimon, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 60 days.

(21) Appl. No.: 09/919,870

(22) Filed: Aug. 2, 2001

(65) Prior Publication Data

US 2002/0014589 A1 Feb. 7, 2002

(30) Foreign Application Priority Data

Aug. 7, 2000 (JP) ........................................ 2000-238452

(51) Int. Cl.$^7$ ............................................. H01J 37/285
(52) U.S. Cl. ........................................ 250/306; 250/307
(58) Field of Search ................................. 250/306, 311, 250/307; 359/483, 484, 490; 315/507

(56) References Cited

U.S. PATENT DOCUMENTS

| | | | |
|---|---|---|---|
| 4,849,629 A | 7/1989 | Daimon et al. | 250/305 |
| 5,107,111 A | 4/1992 | Daimon et al. | 252/205 |
| 5,714,850 A * | 2/1998 | Kitamura et al. | 315/507 |

FOREIGN PATENT DOCUMENTS

EP       0513776 A2 * 11/1992

* cited by examiner

Primary Examiner—Judy Nguyen
Assistant Examiner—Lam Nguyen
(74) Attorney, Agent, or Firm—Armstrong, Westerman & Hattori, LLP

(57) ABSTRACT

Forward scattering peaks of photoelectrons having different angular momenta is generated by radiating to a sample two rays of circularly polarized light that differ in a rotary direction. Two images of photoelectron diffraction patterns are formed by two-dimensionally detecting the photoelectron diffraction patterns formed with the photoelectron forward scattering peaks. The observer can three-dimensionally observe the structure in an atomic arrangement by observing these photoelectron diffraction pattern images with his or hers right and left eyes, respectively.

3 Claims, 6 Drawing Sheets

THREE-DIMENSIONAL ATOM MICROSCOPE, THREE-DIMENSIONAL OBSERVATION METHOD OF ATOMIC ARRANGEMENT, AND STEREOSCOPIC MEASURING METHOD OF ATOMIC ARRANGEMENT

BACKGROUND OF THE INVENTION

1. Field of the Invention

The present invention relates to making it possible for an observer to visually observe a structure of an atomic arrangement three-dimensionally.

2. Description of the Prior Art

A microscope that makes it possible to see a structure of an atomic arrangement directly by an observer's eyes three-dimensionally is not realized yet. Although an electron microscope gives a projection image of an atomic arrangement, it cannot give a stereoscopic image. Moreover, although a scanning tunneling microscope (STM) can give the concavo-convex image of the atomic arrangement on the front face of a sample, the information about the positional relation between a surface atom and an atom thereunder cannot be given.

As described above, although those conventional microscopes make it possible to observe the structure of an atomic arrangement superficially, it does not make it possible to observe the structure of an atomic arrangement three-dimensionally.

As a method for observing atomic structure three-dimensionally, it is possible that an arrangement among atoms is measured or presumed on the basis of various kinds of observation data, and the result is visualized by computer graphics. However, in this technique, since it is necessary to obtain necessary various observation data in quest of the exact positional relation about all the atoms in an observation part, data processing takes time, and hence real time observation becomes difficult.

OBJECTS AND SUMMARY OF THE INVENTION

An object of the present invention is to provide a method and an apparatus for observing the structure of an atomic arrangement with an observer's eyes three-dimensionally.

In order to attain the above-described object, a three-dimensional observation method of an atomic arrangement according to the present invention includes: a step of radiating two rays of circularly polarized light, which differ in a rotary direction, to a sample; a step of forming two photoelectron diffraction patterns that differ in a formative direction of photoelectron forward scattering peaks in circular dichroism generated by the radiation; and a step of obtaining, from those photoelectron diffraction patterns, atomic arrangement images having right-handed and left-handed parallactic angles.

Moreover, a microscope according to the present invention that enables three-dimensional observation of an atomic arrangement comprises: circularly polarized light radiation means for radiating a ray of circularly polarized light to a sample to generate photoelectrons; and two-dimensional detection means for detecting a photoelectron diffraction pattern formed by photoelectron forward scattering peaks with circular dichroism generated by the radiated ray of circularly polarized light two-dimensionally.

Furthermore, a stereoscopic measuring method according to the present invention that enables three-dimensional observation of an atomic arrangement includes: a step of radiating two rays of circularly polarized light, which differ in a rotary direction, to a sample; a step of forming two photoelectron diffraction patterns, which differ in a formative direction of the photoelectron forward scattering peaks in circular dichroism generated by the radiation; and a step of picking up those photoelectron diffraction patterns as photographic images corresponding to a parallactic angle of right-handed and left-handed eyes.

Generally, when a ray of light is radiated to a sample, photoelectrons are emitted from an atom (emitting atom), and the emitted photoelectrons are scattered by a surrounding atom (scattering atom), and generate a forward scattering peak in a direction of connecting the emitting atom and the scattering atom. When the ray of light which irradiates a sample is a ray of circularly polarized light, the direction of a forward scattering peak shifts from the direction of connecting the emitting atom and the scattering atom according to the angular momentum which the ray of circularly polarized light has. The direction where this peak shifts depends on whether the rotary direction of the ray of circularly polarized light is the right or the left (namely, right-handed circularly polarized light or left-handed circularly-polarized light). An atomic arrangement can be three-dimensionally observed by associating two images, which are shifted by these rays of circularly polarized light, with respective images when observing objects with both eyes.

Moreover, a magnification by the three-dimensional observation according to the present invention can be set on the basis of the fact that a parallactic angle at the time of observing an object with both eyes and a parallactic angle of the images obtained with using the circular dichroism in photoelectron diffraction differ by a multiple, not depending on an angle.

Circularly polarized light radiation means for radiating a ray of circularly polarized light to a sample makes photoelectrons with different angular momenta emitted by switching a rotary direction of the ray of circularly polarized light with a ray of right-handed circularly polarized light and a ray of left-handed circularly-polarized light. Two (circular dichroism) photoelectron diffraction patterns that the photoelectrons with different angular momenta form correspond to the diffraction patterns when the atomic arrangement is observed from different directions. An object is observable as a stereoscopic image by observing these two diffraction patterns with both eyes, respectively.

Moreover, by launching the ray of circularly polarized light at a shallow angle to a sample, the angle dependency of a parallactic angle comes to be in agreement with an actual thing, and can obtain a stereoscopic image with little distortion. In addition, it is possible to use synchrotron for a right-handed and left-handed circularly polarized light generating apparatus consisting of an electron storage ring and a circularly polarized light undulator, as circularly polarized light radiation means. The observation precision of an atomic arrangement can be improved by radiating to a sample a ray of circularly polarized light with high energy that is obtained in the synchrotron radiation institution "SPring-8" which the Japan Atomic Energy Research Institute and the Institute of Physical and Chemical Research in Japan have jointly built.

Two-dimensional electron detection means for two-dimensionally detecting a photoelectron diffraction pattern formed by photoelectron forward scattering peaks with the circular dichroism that is generated by a ray of circularly polarized light radiated by the above-described circularly-polarized light radiation means can display the detected photoelectron diffraction pattern on display means as an image and can also form the pattern as a photographic image. In addition, as the two-dimensional photoelectron detection means, it is simplest to use a two-dimensional display-type analyzer such as a two-dimensional display-type spherical mirror analyzer. Nevertheless, a two-dimensional photoelectron diffraction pattern may be detected by moving a one-dimensional or zero-dimensional (detecting only a certain angle) analyzer, or by combining a one-dimensional or zero-dimensional analyzer and one-dimensional or two-dimensional rotation of a sample.

Moreover, the real time observation of an atomic arrangement is achieved by switching the rays of right-handed and left-handed circularly polarized light by the circularly polarized light radiation means at high speed. At this time, in the two-dimensional photoelectron detection means, two photoelectron diffraction patterns can be detected with synchronization with the switching of rays of circularly polarized light, and the variance of the atomic arrangement can be observed in real time by displaying the image.

BRIEF DESCRIPTION OF THE DRAWINGS

The foregoing and other objects and features of the invention will become apparent from the following description of preferred embodiments of the invention with reference to the accompanying drawings, in which.

DETAILED DESCRIPTION OF THE PREFERRED EMBODIMENTS

Figure 1:
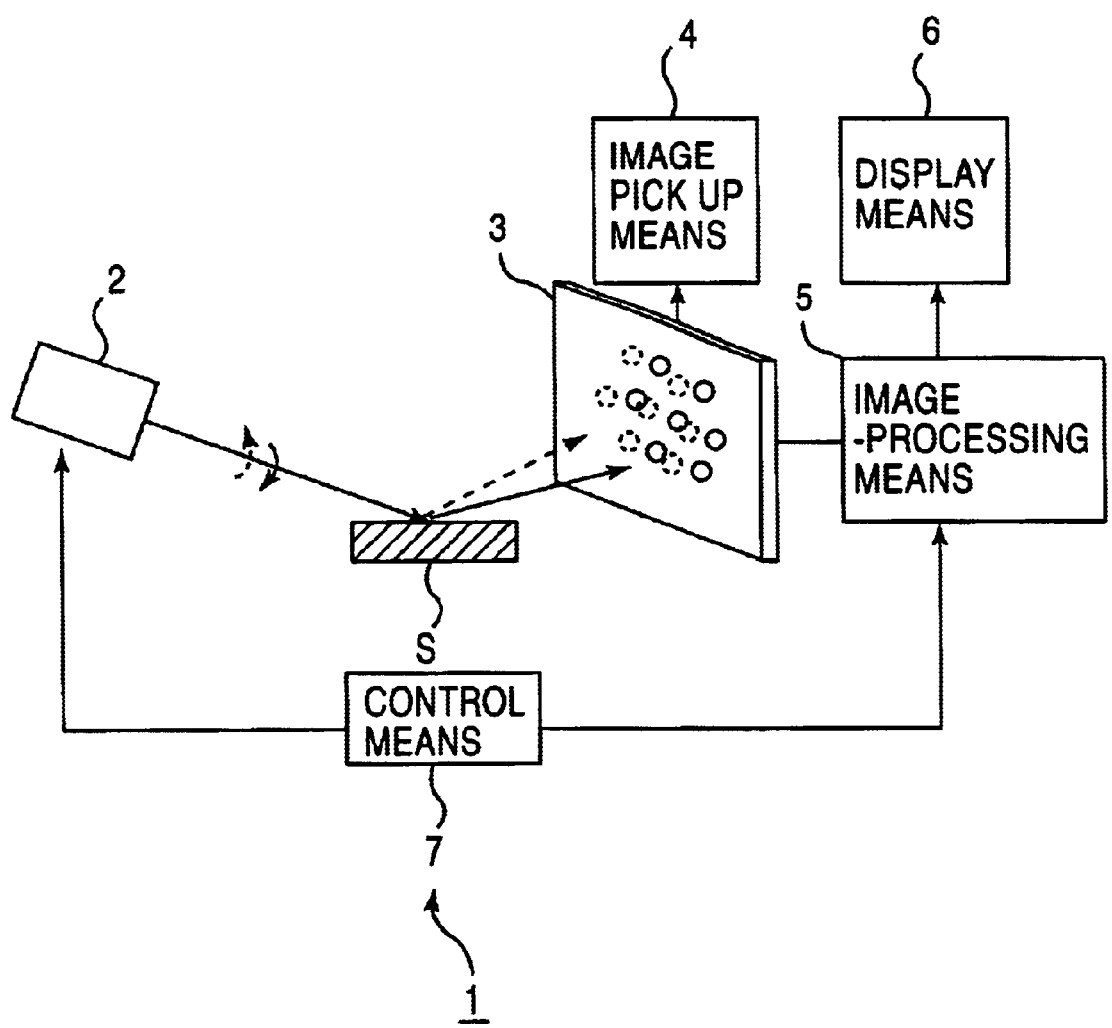
FIG. 1 is an explanatory diagram of a three-dimensional atom microscope according to the present invention.

FIG. 1 is a schematic diagram for explaining a three-dimensional atom microscope according to the present invention.

A three-dimensional atom microscope 1 comprises circularly polarized light radiation means 2, two-dimensional photoelectron detection means 3, image pickup means 4, image-processing means 5, display means 6, and control means 7.

The circularly polarized light radiation means 2 forms two rays of circularly polarized light (a ray of right-handed circularly-polarized light and a ray of left-handed circularly-polarized light) that differ in a rotary direction, and radiate them to a sample S. As for the irradiation to the sample S with these two rays of circularly polarized light, it is possible to form and radiate a ray of circularly polarized light in a certain rotary direction (for example, a ray of left-handed circularly-polarized light) first, and to form and radiate a ray of circularly polarized light in another direction (for example, a ray of right-handed circularly-polarized light) by switching the direction of the ray of circularly polarized light.

The circularly polarized light radiation means 2 may be, for example, a synchrotron, or a right-handed and left-handed circularly-polarized light generating apparatus consisting of an electron storage ring and a circularly polarized light undulator. Moreover, a synchrotron radiation facility such as "SPring-8" will give high energy ray of circularly polarized light, thus improving the observation precision of an atomic arrangement.

The two-dimensional photoelectron detection means 3 detects two-dimensionally photoelectrons generated by radiation of two rays of circularly polarized light, whose rotary directions are different, from the circularly polarized light radiation means 2, and obtains two photoelectron diffraction patterns. These photoelectron diffraction patterns obtained express an atomic arrangement in the radiation positions of the rays of circularly polarized light.

Two photoelectron diffraction patterns obtained by the two-dimensional photoelectron detection means 3 are made to be photographic images by the image pickup means 4 respectively. An observer, as described later, can observe the atomic arrangement three-dimensionally by observing the photograph images of these two photoelectron diffraction patterns with the left eye and the right eye respectively.

The image-processing of the two photoelectron diffraction patterns obtained by the two-dimensional photoelectron detection means 3 is performed by the image-processing means 5, display means 6, and control means 7, so that the two photoelectron diffraction patterns are recorded or displayed as image data. The image-processing means 5 may include the image processing of correcting the distortion of an image by the two-dimensional photoelectron detection means 3 and the like. The control means 7 controls the switching of the rotary direction of a ray of circularly polarized light in the circularly polarized light radiation means 2, and controls the image-processing means 5 according to the switching of the rotary direction. An observer can observe an atomic arrangement three-dimensionally by observing the images of two photoelectron diffraction patterns displayed on the display means 6 with the left eye and the right eye, respectively.

As the two-dimensional photoelectron detection means 3, a two-dimensional display-type analyzer such as a two-dimensional display-type spherical mirror analyzer can be used. A stereoscopic image and a stereograph can be obtained without correcting distortion since there is no distortion of the image in case of using the two-dimensional display-type spherical mirror analyzer.

Figure 2:
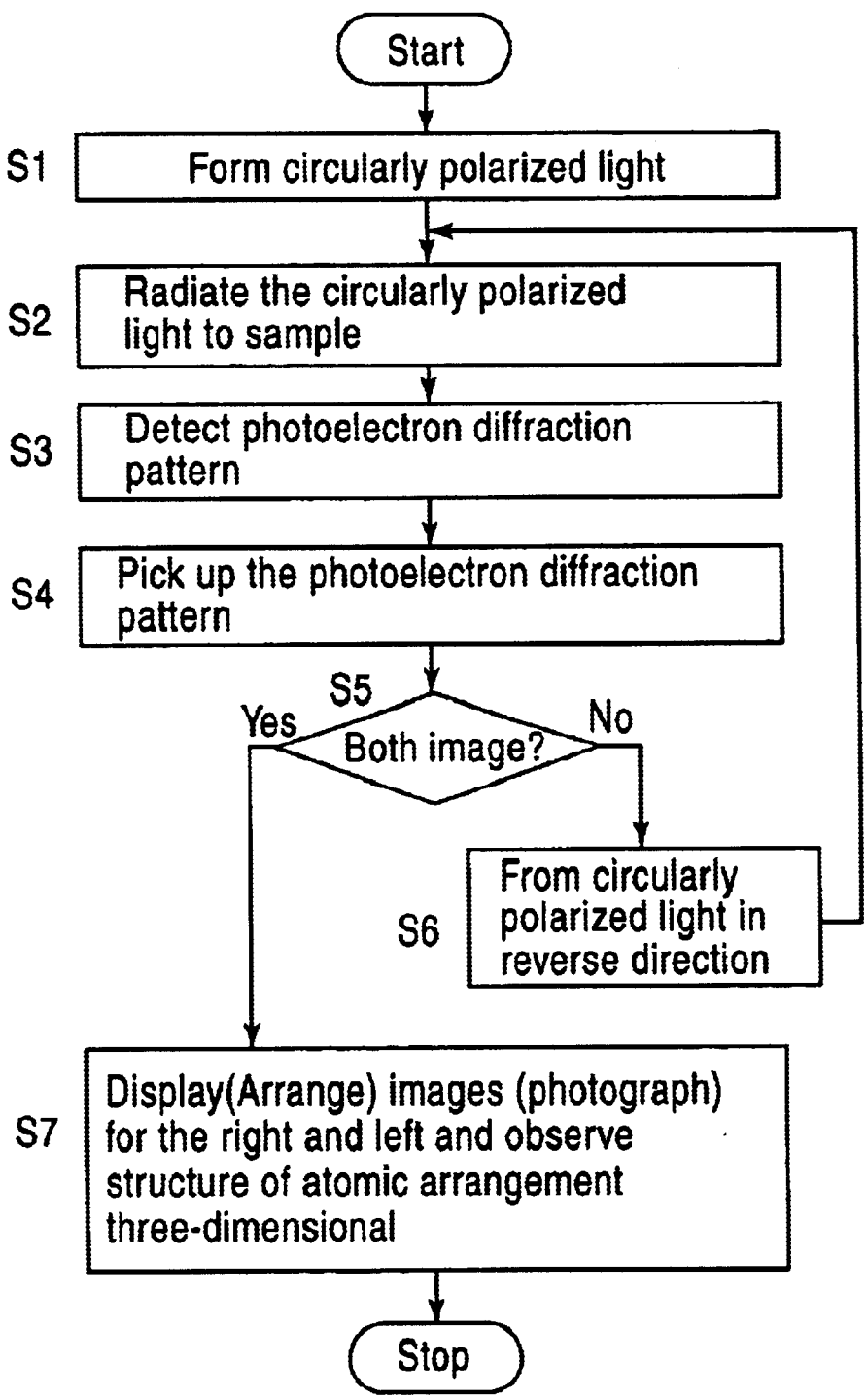
FIG. 2 is a flow chart showing the procedure of three-dimensional observation of atomic arrangement structure according to the present invention.

Next, the procedure of three-dimensional observation of an atomic arrangement according to the present invention will be described on the basis of a flow chart shown in FIG. 2.

First, a ray of circularly polarized light in any one of the right-handed and left-handed rotary directions is formed by the circularly polarized light radiation means 2 (step S1). The circularly polarized light formed is radiated at the sample S (Step S2). The ray of circularly polarized light to be radiated has the energy of, for example, about 800 eV–1 keV, and makes a photoelectron with the kinetic energy of hundreds or more eV (for example, 400 eV–500 eV) emitted by being absorbed in each atom (emitting atom) of the sample S.

The photoelectron emitted by the ray of circularly polarized light from a certain atom (emitting atom), receiving angular momentum from the ray of circularly polarized light and rotating, is incident to a surrounding atom (scattering atom) in an atomic arrangement at a certain angle (deviation angle) shifted from the direction of connecting the emitting atom and the scattering atom. The photoelectrons being incident to this scattering atom are scattered about by the scattering atom, and generate a forward scattering peak in the direction, shifted by the above-described deviation angle from the direction of connecting the emitting atom and the scattering atom. A photoelectron diffraction pattern is formed by the forward scattering peaks that are shifted by the above-described deviation angle. The two-dimensional photoelectron detection means 3 detect this photoelectron diffraction pattern (step S3), and the photoelectron diffraction pattern detected is picked up as an image or photograph (step S4).

Next, a ray of circularly polarized light in a rotary direction reverse to that of the ray of circularly polarized light formed at step S1 is formed (steps S5 and S6). Using the ray of circularly polarized light in the reverse rotary direction, processing of the above-described steps S2 to S4 is repeated to obtain a photoelectron diffraction pattern by the ray of circularly polarized light in the reverse rotary direction. Then, images or photographs of two photoelectron diffraction patterns obtained with the rays of circularly polarized light that differ in their rotary directions are obtained. A photoelectron diffraction pattern obtained by the ray of circularly polarized light in the reverse rotary direction has deviation angles in the opposite direction.

As described above, photoelectrons are incident to a scattering atom at a predetermined deviation angle from two respectively opposite positions, so that two photoelectron diffraction patterns are obtained. Then, an image for the left (or photograph for the left) and an image for the right (or photograph for the right) are formed from two photoelectron diffraction patterns.

Then, the image for the left (or photograph for the left) and the image for the right (or photograph for the right) are displayed (or arranged) to form a stereoscopic image (or stereograph). The stereoscopic images (or stereographs) displayed (or arranged) correspond to the images (or photographs) obtained by observing the atomic arrangement from the positions shifting to the right and left. Hence, it is possible to observe the atomic arrangement three-dimensionally by observing respective images (photographs) with the left eye and the right eye (step S7).

Next, it will be described with reference to FIGS. 3 to 6D that two images (photographs) obtained by the present invention express the structure of an atomic arrangement three-dimensionally.

Figure 3:
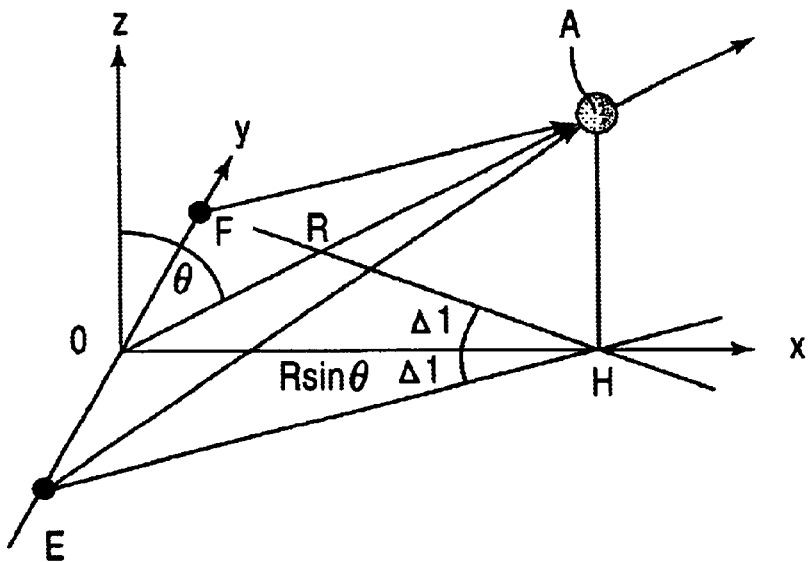
FIG. 3 is a diagram for explaining a parallactic angle when observing an object A with an observer's right and left eyes.

FIG. 3 is a diagram for explaining a parallactic angle when observing an object in three-dimensional space with an observer's right and left eyes.

In FIG. 3, it is assumed that a right eye E and a left eye F of an observer are at the points −b and +b on the y-axis, and that an observer's face faces in the direction of the x-axis and the observer's head faces in the direction of the z-axis. The position of the object A observed by this observer is expressed in polar coordinates as (R, θ, φ). Here, R is a distance from the origin O (center point of the right and left eyes E and F) to the object A, θ is an angle formed with the z-axis and a line segment OA, and φ is an angle formed with the x-axis and a segment OH that is formed by projecting the line segment OA on the x-y plane. In the case of FIG. 3, φ=0.

When the observer observes the object A, which is at (R, θ, 0) in polar coordinate notation, with his/her right and left eyes E and F, a parallactic angle Δ1 is expressed as follows:

$$\Delta 1 = \arctan\{b/(R \cdot \sin\theta)\} \quad (1)$$

Here, a space between the observer's right and left eyes E and F is set to be 2b. In FIG. 3, the parallactic angle Δ1 is an angle OHE or an angle OHF.

Figure 4:
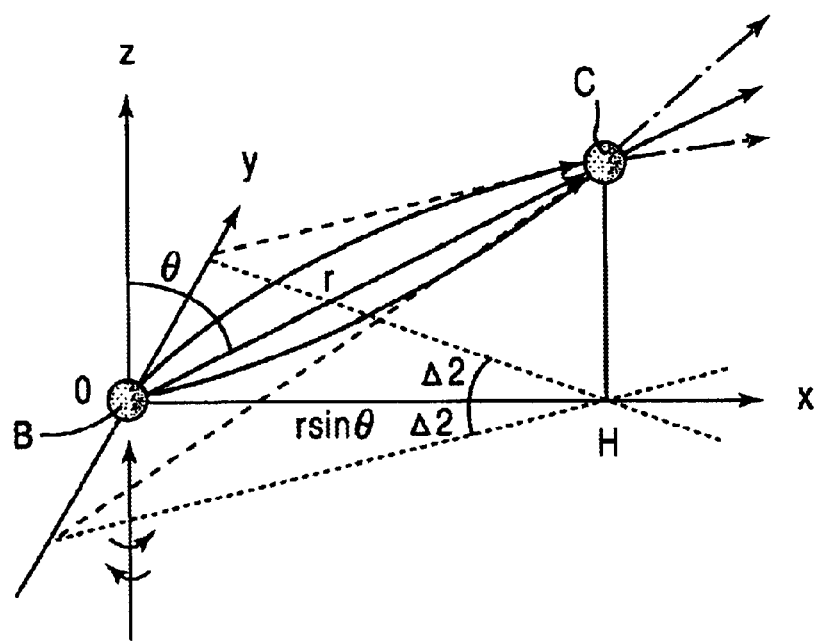
FIG. 4 is a diagram for explaining a photoelectron being emitted when a ray of circularly polarized light is radiated to an atom (emitting atom B), and the emitted photoelectron being scattered by a surrounding atom (scattering atom C), and generating a forward scattering peak.

FIG. 4 is a diagram for explaining a deviation angle when a photoelectron emitted from a emitting atom is incident to a scattering atom.

In FIG. 4, when a ray of circularly polarized light is radiated in the plus direction of the z-axis to an atom B positioned at the origin O, a photoelectron is emitted from this atom B (emitting atom). Then, this emitted photoelectron, receiving angular momentum from the ray of circularly polarized light and rotating, is incident to a surrounding atom C. At this time, the photoelectron is scattered by this atom C (scattering atom), and generates a forward scattering peak. The direction of the forward scattering peak of this photoelectron shifts by a certain angle from the direction of connecting the emitting atom B and the scattering atom C owing to the angular momentum that the ray of circularly polarized light has. Let the position of the scattering atom C be (r, θ, 0) in polar coordinate notation, then this deviation angle Δ2 is expressed as follows:

$$\Delta 2 = \arctan\{m/(k \cdot r \cdot \sin^2\theta)\} \quad (2)$$

Here, m is a quantum number representing a z component of the angular momentum of a photoelectron (that is, magnetic quantum number), and k is a wave number.

In the above formula (2), k (wave number) is a constant and is not dependent on θ. On the other hand, m (magnetic quantum number) is dependent on θ, and in the case of a W4f (one of electron orbits of tungsten) photoelectron etc., m≈α sin θ (α is a proportional constant).

Therefore, in this case, the above formula (2) is expressed as follows:

$$\Delta 2 = \arctan\{(\alpha/k)/(r \cdot \sin\theta)\} \quad (2')$$

Then, by comparing the above formula (1) of a parallactic angle Δ1 with the above formula (2') of a deviation angle Δ2, it becomes clear that both formulas are equivalent just except the difference of the constants b (the former) and α/k (the latter). That is, the deviation angle Δ2 can be treated as the parallactic angle Δ1.

Therefore, it is possible to three-dimensionally observe the arrangement structure of scattering atoms, which contributes to photoelectron diffraction patterns, by observing with an observer's right and left eyes with each deviation angle Δ2 of two photoelectron diffraction patterns serving as a parallactic angle.

Three-dimensional observation of the structure of an atomic arrangement by treating the deviation angle Δ2 as a parallactic angle will be explained below using FIGS. 5A and 5B.

Figure 5A:
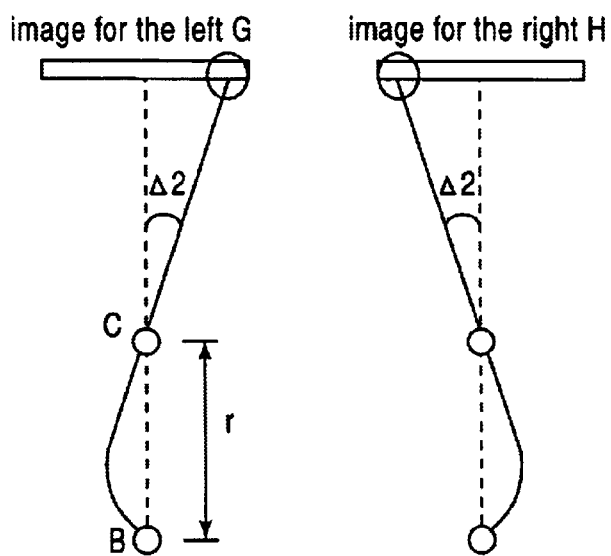
FIGS. 5A and 5B are diagrams for explaining three-dimensional observation of an object and a magnification of an image of the object by associating a deviation angle ($\Delta 2$) of the photoelectron, which is shown in FIG. 4 and is caused by a ray of circularly polarized light, with the parallactic angle ($\Delta 1$) shown in FIG. 3.

FIG. 5A typically shows a deviation angle of a photoelectron diffraction pattern due to the dichroism of a circularly polarized light. The photoelectron emitted from the emitting atom B is incident to the scattering atom C at the deviation angle Δ2 owing to having angular momentum. The photoelectron diffraction pattern is mainly formed from the forward scattering peaks of the scattering atoms such as C, and the deviation angle of the peaks in this photoelectron diffraction pattern image also becomes Δ2 and so on.

Figure 5B:
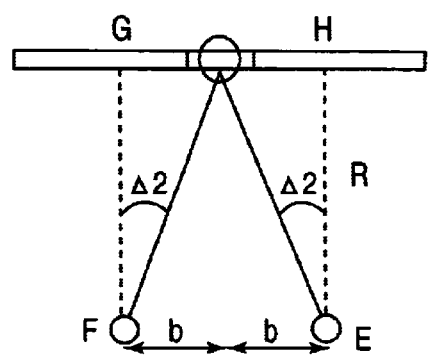

FIG. 5B shows that a photoelectron diffraction pattern image is observed with an observer's eye. In an observation of an atomic arrangement using photoelectron diffraction pattern image, the photoelectron diffraction pattern images for the right and the left are placed away from the eyes E and F by a distance, respectively, and then positioned so that the range of measurement angle of those photoelectron diffraction patterns coincides with the angular extension arising when observing those patterns images with the eyes.

If those photoelectron diffraction pattern images are positioned in such a manner as described above, a deviation angle Δ2 comes to a palallactic angle assumed when observing those images (or photographs) with the eyes. For three-dimensional recognition of an atom, as illustrated in FIG. 5B, the direction of both the eyes are shifted so that the image of the atom in the image G for the left and the image of the atom in the image H for the right overlap each other when observing the left eye F and the right eye E. In this way, as illustrated in FIG. 5B, the atom is observed at a position apart from the right eyes E and the left eyes F by a distance R. This distance R is obtained from the above-described formula (1) as follows:

$$R=b/(\tan \Delta 2 \cdot \sin \theta) \quad (3)$$

Here, the distance between an observer's right eye E and left eye F is set to be $2b$.

In this manner, the structure of an atomic arrangement can be three-dimensionally observed by observing photoelectron diffraction pattern images for the left and right with left and right eyes, respectively.

A magnification with which an observer observes a photoelectron diffraction pattern image with the observer's eyes is determined by a ratio (R/r) of R in formula (1) to r in formula (2'). This r is shown in FIG. 5A, and R is shown in FIG. 5B. Then, the magnification R/r is given in the following formula from formula (1) and formula (2'), assuming $\Delta 1 = \Delta 2$, $$R/r=(k \cdot b)/\alpha \quad (4)$$

The right-hand side of this formula (4) expresses the magnification applied when observing the structure of an atomic arrangement three-dimensionally according to the method of the present invention. In the case of the above-described W4f atomic arrangement, the magnification (R/r) is about $2 \times 10^{10}$.

The formula (2) shows that the value of a parallactic angle $\Delta 2$ for an atom will change if the atom lies at a different position. Thus, assuming that the parallactic angle for the atom is $\Delta 2'$, the distance R' an observer recognizes is determined by the formula, $R'=b/(\tan \Delta 2 \cdot \sin \theta)$. In this case, too, the magnification remain unchanged according to the formula (4), with the relative positional relation of the atoms observed remaining unchanged.

FIGS. 6A to 6D show an example of detection according to the present invention.

Figure 6A:
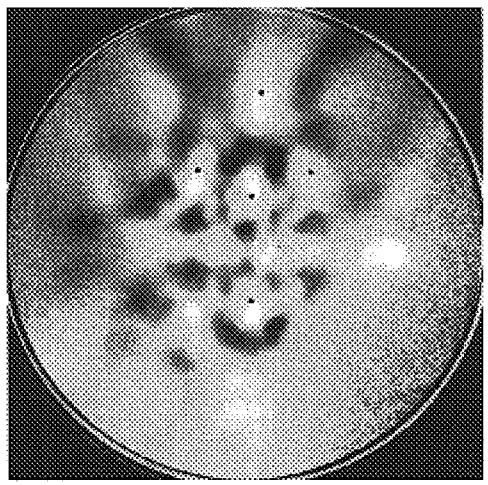
FIGS. 6A to 6D show a detection example according to the present invention.
Figure 6B:
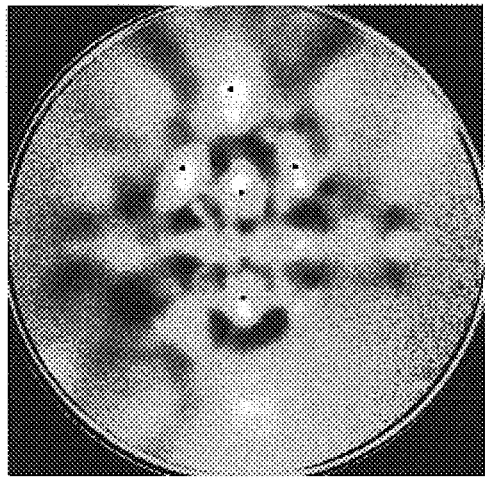
Figure 6C:
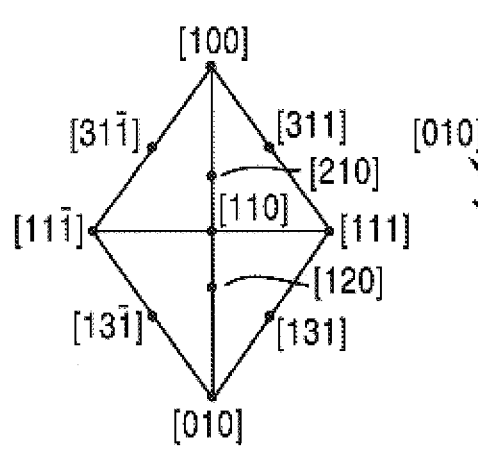

FIGS. 6A and 6B show images of diffraction patterns of W4f photoelectrons which are emitted from the plane (110) of tungsten W and have kinetic energy of 800 eV. Moreover, FIG. 6A shows a photoelectron diffraction pattern image for the left and FIG. 6B shows the pattern image for the right, and rotary directions of their rays of circularly polarized light are different. FIG. 6C typically shows the directions of crystallographic axes corresponding to FIGS. 6A and 6B. In FIGS. 6A and 6B, forward scattering peaks are observed in the directions of crystallographic axes such as [100], [111], [311], and [210].

Positions of the forward scattering peaks displayed in the images shown in FIGS. 6A and 6B shift from the positions of crystallographic axes shown in FIG. 6C to the right and left. When these deviations become the same as the parallactic angle of the images of an object and an observer observes these images with the observer's right and left eyes, the object can be three-dimensionally observed.

Figure 6D:
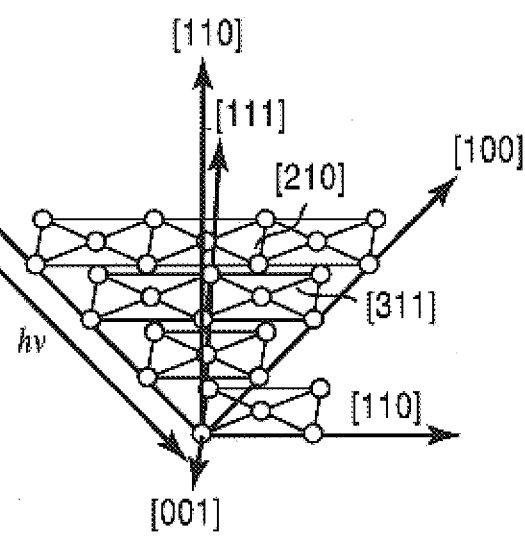

FIG. 6D typically shows the relation among the directions such as [100], [111], [311], and [210]. A ray of circularly polarized light radiates from the direction [010] to the plane (110).

Figure 7:
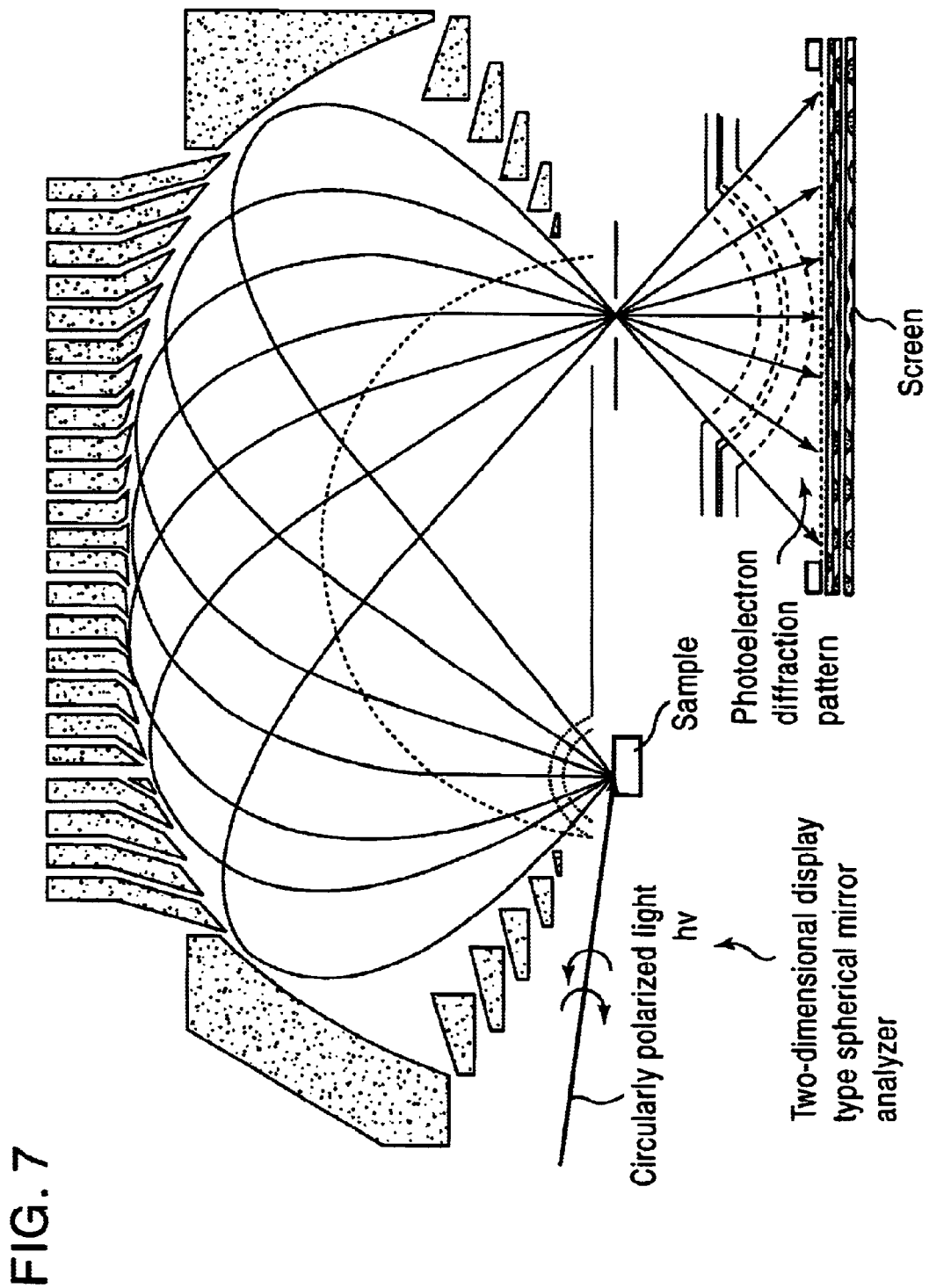
FIG. 7 is a schematic diagram showing the outline of the structure of a two-dimensional display-type spherical mirror analyzer.

FIG. 7 shows the schematic structure of a two-dimensional display type spherical mirror analyzer that is an example of two-dimensional photoelectron detection means.

The two-dimensional display type spherical mirror analyzer makes a photoelectron diffraction pattern displayed on a two-dimensional detection face (screen) in the condition where a diffracted photoelectron is reflected by a virtual spherical mirror. In this two-dimensional display type spherical mirror analyzer, a ray of circularly polarized light is incident to a sample at an angle as gentle as possible. Owing to this, the emission angle dependency of a magnetic quantum number m is substantially proportional to $\sin \theta$, and a stereoscopic image without distortion can be obtained.

According to this embodiment of the present invention, it becomes possible to perform observation equivalent to observing an atomic arrangement with right and left eyes.

Moreover, a real time detection can be performed by switching the rotary direction of a ray of circularly polarized light at high speed.

As explained above, according to the three-dimensional atom microscope and the three-dimensional observation method according to the present invention, the structure of an atomic arrangement can be three-dimensionally observed directly with eyes. Moreover, according to the measuring method of the present invention, a stereograph suitable for three-dimensional observation can be obtained.

What is claimed is:

1. A three-dimensional atom microscope, comprising:
   circularly polarized light radiation means for radiating two rays of circularly polarized light, which differ in rotary direction, onto a sample to generate photoelectrons; and
   two-dimensional photoelectron detection means for two-dimensionally detecting two respective photoelectron diffraction patterns formed by photoelectron forward scattering peaks with circular dichroism generated by the radiated circularly polarized light.

2. A three-dimensional observation method of a structure of an atomic arrangement, comprising:
   a step of radiating two rays of circularly polarized light, which differ in a rotary direction, to a sample;
   a step of forming two photoelectron diffraction patterns which differ in a formative direction of photoelectron forward scattering peaks of circular dichroism generated by the radiation; and
   a step of obtaining atomic arrangement images having right-handed and left-handed parallactic angles from those photoelectron diffraction patterns.

3. A stereoscopic measuring method of an atomic arrangement, comprising:
   a step of radiating two rays of circularly polarized light, which differ in a rotary direction, to a sample;
   a step of forming two photoelectron diffraction patterns, which differ in the formative direction of the photoelectron forward scattering peaks of circular dichroism generated by the radiation; and
   a step of picking up those photoelectron diffraction patterns as photographic images corresponding to right-handed and left-handed parallactic angles.

* * * * *